US00PP36099P2

(12) United States Plant Patent
Aguilar Morán

(10) Patent No.: US PP36,099 P2
(45) Date of Patent: Sep. 10, 2024

(54) DESSERT BANANA PLANT NAMED 'HG07'

(50) Latin Name: *Musa acuminata*
Varietal Denomination: HG07

(71) Applicant: Fundación Hondureña de Investigación Agrícola (FHIA), San Pedro Sula (CN)

(72) Inventor: Juan Fernando Aguilar Morán, La Lima (HN)

(73) Assignee: Fundación Hondureña de Investigación Agrícola (FHIA) (HN)

( * ) Notice: Subject to any disclaimer, the term of this patent is extended or adjusted under 35 U.S.C. 154(b) by 0 days.

(21) Appl. No.: 18/469,787

(22) Filed: Sep. 19, 2023

(51) Int. Cl.
*A01H 5/08* (2018.01)
*A01H 6/00* (2018.01)

(52) U.S. Cl.
USPC ..... Plt./160

(58) Field of Classification Search
USPC ..... Plt./156, 160
See application file for complete search history.

*Primary Examiner* — Susan McCormick Ewoldt
(74) *Attorney, Agent, or Firm* — Garvey, Smith & Nehrbass, Patent Attorneys, L.L.C.; Seth M. Nehrbass; Fabian M. Nehrbass

(57) ABSTRACT

'HG07' is a hybrid dessert banana variety with a tall stature, is tolerant to Black Sigatoka, and produces high-quality fruit.

6 Drawing Sheets

Latin name of the genus and species of the plant claimed: *Musa acuminata.*

Variety denomination: 'HG07.'

CROSS-REFERENCE TO RELATED APPLICATIONS

This application is co-pending with the following additional applications by the same inventor: "DESSERT BANANA PLANT NAMED 'SH-4199'" (patent application Ser. No. 18/469,772), "DESSERT BANANA PLANT NAMED 'WW01'" (patent application Ser. No. 18/469,766), "DESSERT BANANA PLANT NAMED 'NW02'" (patent application Ser. No. 18/469,776), and "DESSERT BANANA PLANT NAMED 'WH02'" (patent application Ser. No. 18/469,781). The plants of these applications, as well as the plant of the present application, were created in the banana breeding program of Applicant/Owner/Assignee, FHIA.

STATEMENT REGARDING FEDERALLY SPONSORED RESEARCH OR DEVELOPMENT

Not applicable.

BACKGROUND OF THE INVENTION

This invention relates to a new and distinctive hybrid banana variety named 'HG07'. This new hybrid variety was the result of a field cross performed in La Lima Cortés, Honduras, between 'HG' x 'HG' (Both unpatented). 'HG' is a triploid plant (AAA) susceptible to Black Sigatoka leaf spot disease and *Fusarium oxysporum* race 1, belonging to the Gros Michel group. 'HG' is a mutant of Gros Michel used in genetic improvement to generate tetraploid mothers; varieties of the Cavendish group replaced this variety due to its susceptibility to fusariosis. In the 20$^{th}$ century, it was one of the world's most commercialized fruits due to its excellent taste and yield.

'HG07' is a tetraploid hybrid (AAAA) created for the genetic improvement of the Gros Michel banana group. This hybrid was selected in 2018 from several first-generation seedlings from the cross between 'HG' x 'HG'. It was chosen as a tetraploid hybrid maintaining the "Gros Michel" type stature and taste of its female parental line and producing bunches of 25 kilograms with fruits of the same quality as their parents. 'HG07' was asexually reproduced by corms in La Lima Cortes, Honduras. All plants and fruit run true to the initially selected plant and are identical in all aspects.

'HG07' is a selection of crosses made between plants of the "HG" variety, inheriting its flavor, cluster shape, and plant structure. The few differences between 'HG07' and its parents can be seen in the shape of the fruit, which is slightly smaller and has shorter fingers. Another important difference is the fertility when used as a mother; 'HG07' is more fertile than its 'HG' parents. The other characteristics are very similar between 'HG07' and its 'HG' parents.

When comparing 'HG07' with a commercial cultivar such as 'Grand Naine' or 'Williams', we can say that there are important characteristic differences such as: the size of the plant, which is superior in 'HG07'; the flavor of commercial varieties is simpler than that of 'HG07'; the commercial varieties and 'HG07' have equal susceptibility to diseases such as Black Sigatoka; and commercial varieties are resistant to *Fusarium oxysporum* f.sp. cubense Race 1, while 'HG07' is susceptible.

BRIEF SUMMARY OF THE INVENTION

'HG07' is a hybrid dessert banana variety with a tall stature, is tolerant to Black Sigatoka, and produces high-quality fruit.

BRIEF DESCRIPTION OF THE PHOTOGRAPHS

The figures describe the characteristics of the 'HG07' hybrid banana variety. The color shown in the photographs is as nearly accurate as reasonably possible in this type's color representation.

FIG. 1 shows the typical appearance of a plant at nine months old;

FIGS. 2A-B shows blotches at the petiole base (A) and a petiole canal leaf (B);

FIGS. 3A-C shows the shape of a leaf blade base (A) and leaf upper (B) and leaf lower (C) surfaces;

FIG. 4 shows typical suckers;

Figure 1:
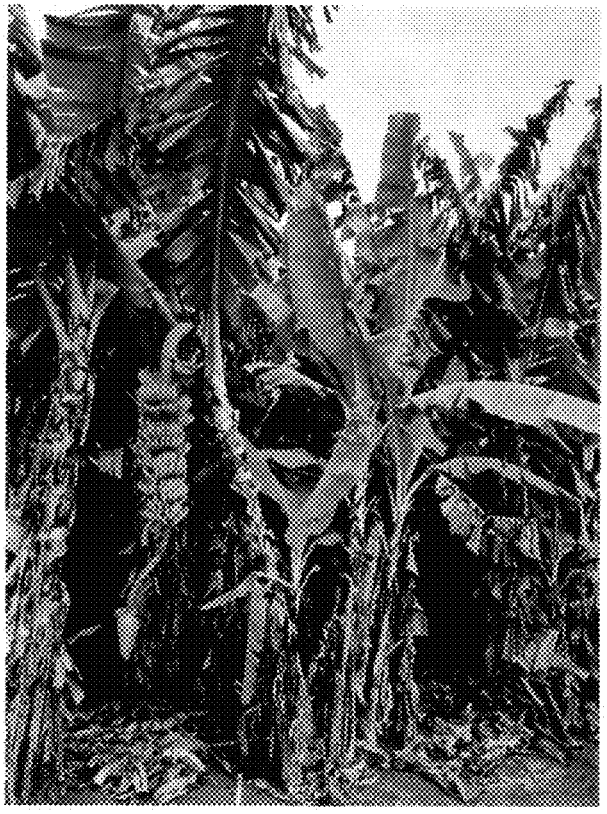
Figures 2A, 2B:
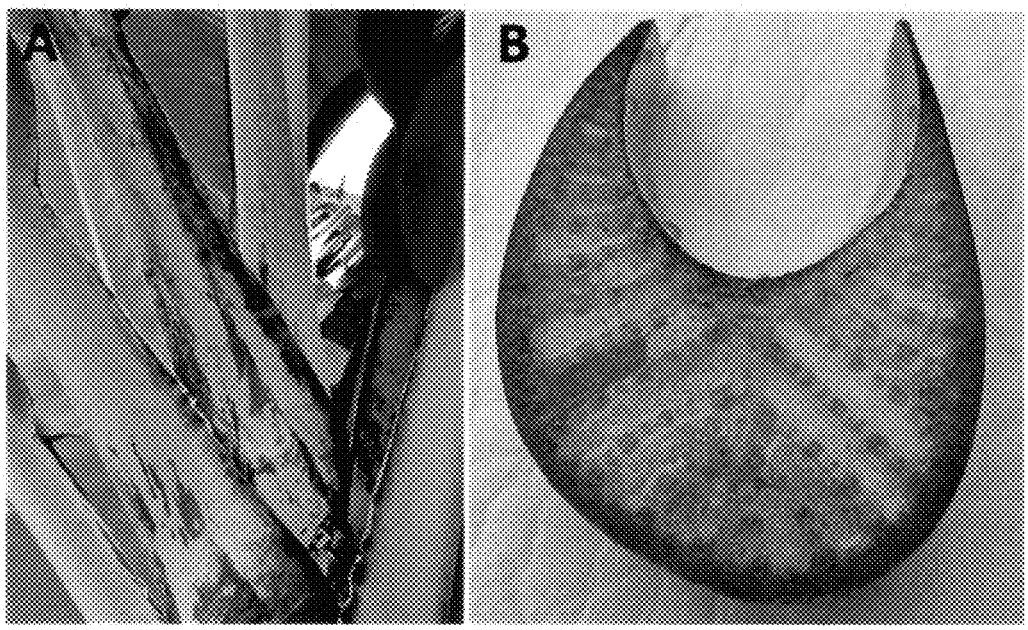
Figure 5:
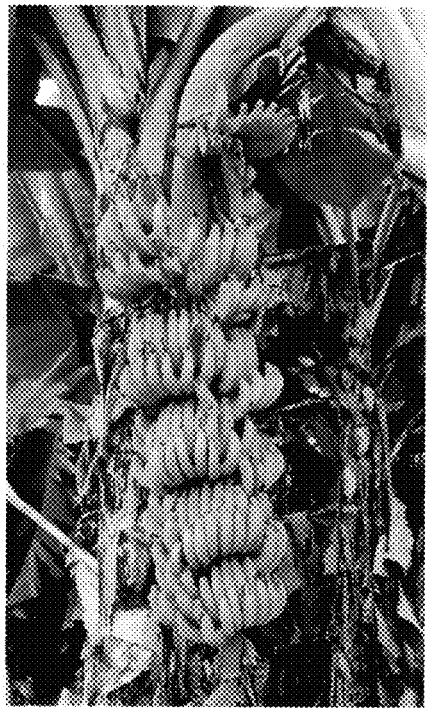
FIG. 5 shows a usual fruit bunch.
Figure 6:
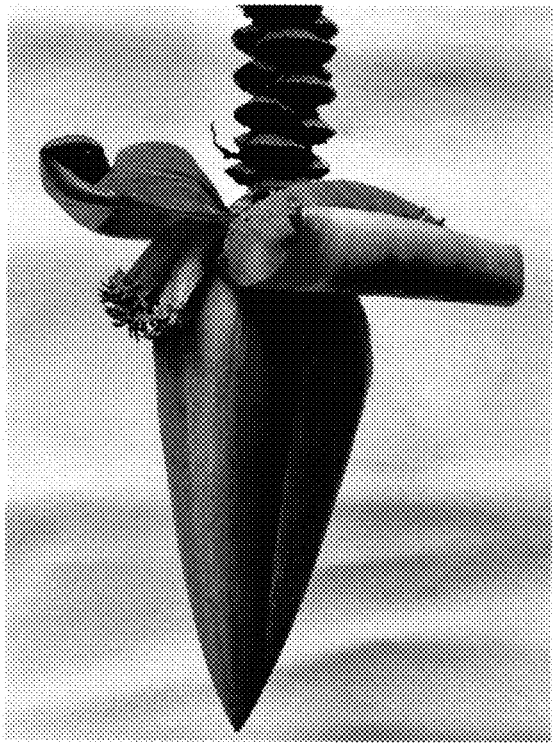
FIG. 6 shows a male bud.
Figure 9:
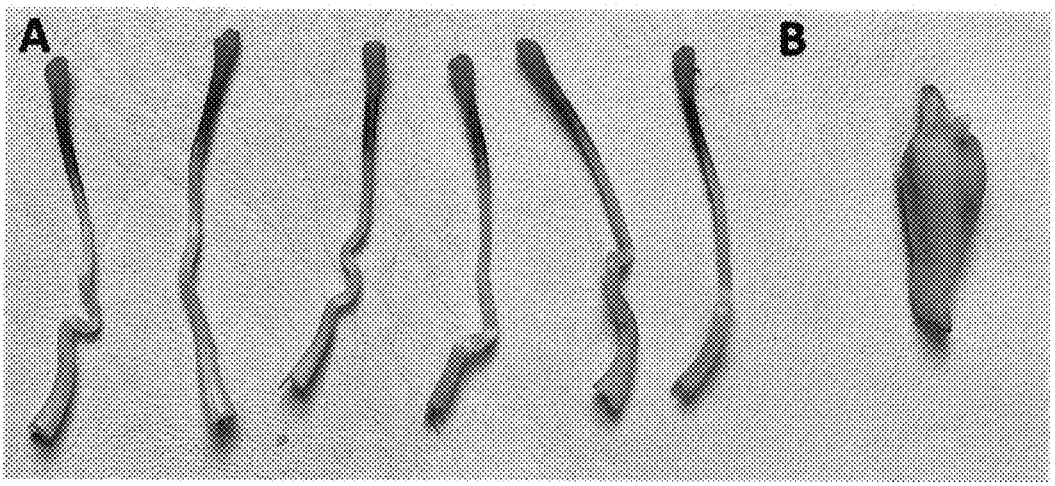
Figure 10:
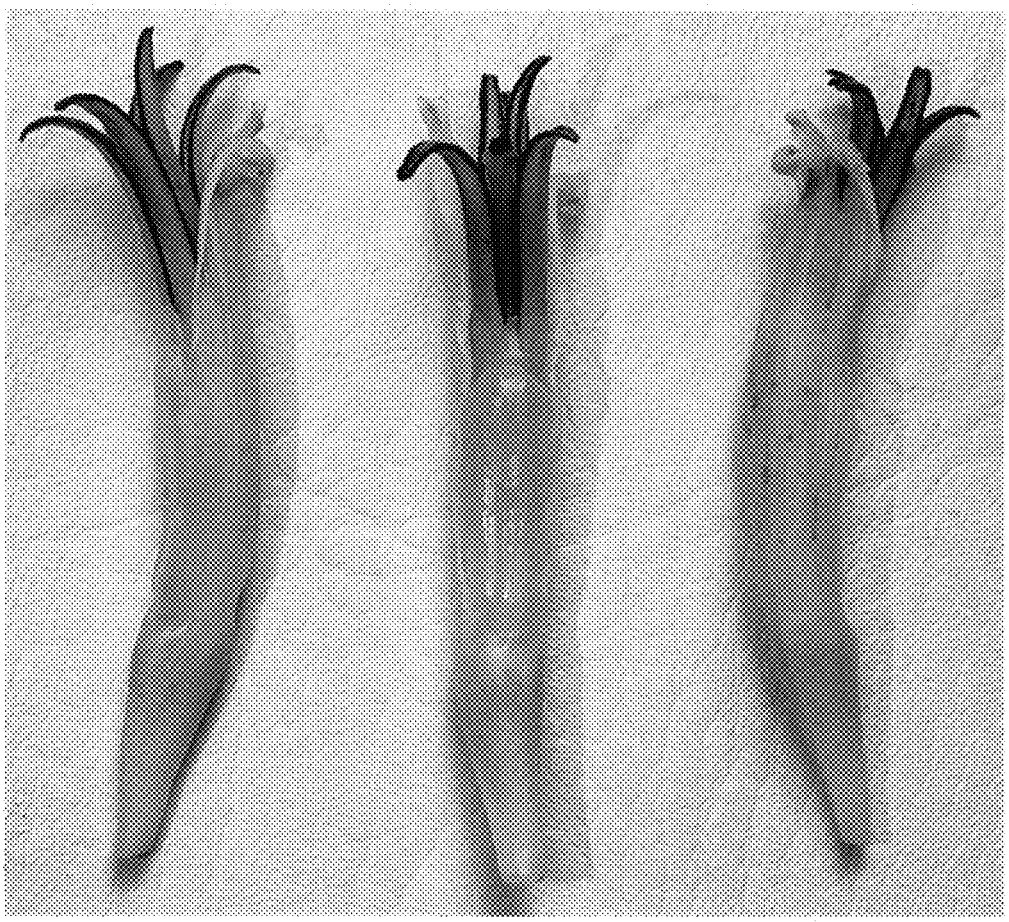
Figure 11:
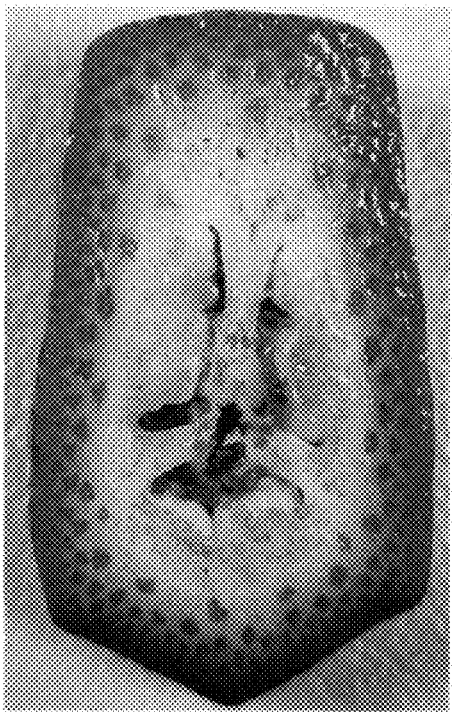

FIGS. 7A-C shows bracts of a male bud;

FIG. 8A-B shows compound tepal (A) and free tepals (B) lobes;

FIG. 9A-B shows style shape (A) and ovary (B);

FIG. 10 shows a typical male flower;

FIG. 11 shows rowed ovules; and

Figure 12:
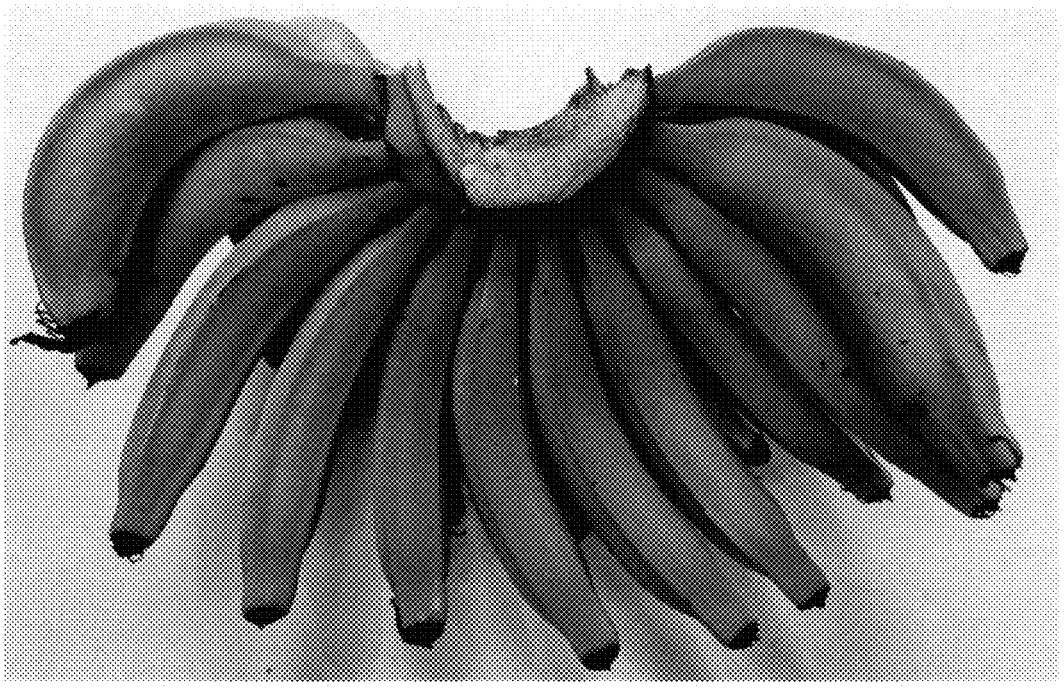

FIG. 12 shows a typical second hand.

DETAILED BOTANICAL DESCRIPTION

The following is a detailed botanical description of the new variety 'HG07' at nine months old. The report is from plants located in La Lima, Cortés, Honduras, that were evaluated in 2023. The descriptions concord with the internationally standardized "Descriptors for Banana (Musa spp.)" elaborated by IPGRI/INIBAP/CIRAD, 1996, and The U.K.'s Royal Horticultural Society's (R.H.S.) Colour Chart, 2001. The 'HG07' plant and its fruit may differ slightly from the detailed descriptors shown below due to variations in cultural practices, soil types, and climatic conditions under which the variety may be cultivated.

TABLE 1

| Botanical Description of 'HG07' | |
|---|---|
| Leaf habit | Intermediate |
| Dwarfism | Normal |
| Pseudostem height | ≥3 (3.2) meters |
| Pseudostem aspect | Normal |
| Pseudostem color | Yellow-Green (N144C, RHS) |
| Pseudostem appearance | Shiny (not waxy) |
| The predominant underlying color of the pseudostem | Blue-Green (112D, RHS) |
| Pigmentation of the underlying pseudostem | Red (46A, RHS) |
| Sap color | Watery (White 155C RHS) |
| Wax-on leaf sheaths | Very Little or no visible sign of wax |
| Number of suckers | 5 |
| Development of suckers | Very good |
| Position of suckers | Close to parent (vertical growth) |
| Blotches at the petiole base | Extensive pigmentation |
| Blotches color | Brown (N200A, RHS) |
| Petiole canal leaf III | Wide with erect margins |
| Petiole margins | Winged and clasping the pseudostem |
| Wing type | Dry, short wings |
| Petiole margin color | Purple (77A, RHS) |
| Edge of petiole margin | Colourless (Without a color line along) |
| Petiole margin width | >1 cm |
| Leaf blade length | 171 to 220 cm |
| Leaf blade width | 71 to 80 cm |

TABLE 1-continued

| Botanical Description of 'HG07' | |
|---|---|
| Petiole length | ≤50 cm |
| Color of the leaf's upper Surface | Green (137B, RHS) |
| Appearance of leaf upper surface | Shiny |
| Color of the leaf's lower surface | Yellow-Green (147B, RHS) |
| The appearance of the leaf's lower surface | Dull |
| Wax on leaves | Very Little or no visible sign of wax |
| The insertion point of the leaf blade on the petiole | Symmetric |
| The shape of the leaf blade base | Both sides rounded |
| Leaf corrugation | Even, smooth |
| Venation pattern | Single centralized |
| Color of midrib dorsal surface | Yellow-Green (144B, RHS) |
| Color of midrib ventral surface | Green-White (157A, RHS) |
| Color of cigar leaf dorsal surface | Green (139C, RHS) |
| Blotches on leaves of water suckers | Without blotches |
| Peduncle length | 31-60 cm |
| Empty nodes on the peduncle | Two or more |
| Peduncle width | 7-12 cm |
| Peduncle color | Yellow-Green (144A, RHS) |
| Peduncle hairiness | Slightly hairy |
| Bunch position | Hanging vertically |
| Bunch shape | Truncated cone shape |
| Bunch appearance | Compact |
| Flowers that form the fruit | Female |
| Fruits | Biseriate |
| Rachis type | Present and male buds may be degenerated or persistent. |
| Rachis position | Failing vertically |
| Rachis appearance | Bare |
| Male bud type | Normal (present) |
| Male bud shape | Intermediate |
| Male bud size | 25-30 cm |
| Bract base shape | Large shoulder |
| Bract apex shape | Slightly Pointed |
| Bract imbrication | Old bracts overlap at the apex of the bud. |
| Color of the bract external face | Greyed-Purple (187A, RHS) |
| Color of the bract internal face | Greyed-Purple (185A, RHS) |
| Color of the bract apex | No tinted with yellow (the color is uniform until apex) |
| Color stripes on the bract | Without discolored lines (not ridges) on the external face |
| Bract scars on rachis | Very prominent |
| Fading of color on bract base | Color discontinuing towards the base. |
| Male bract shape | Ovate |
| Male bract lifting | Lifting two or more at a time |
| Bract behavior before falling | Revolute (Rolling) |
| Wax on the bract | Moderately waxy |
| Presence of grooves on the bract | Moderate |
| Male flower behavior | Falling before the bract |
| Compound tepal basic color | Green-White (157D, RHS) |
| Compound tepal pigmentation | Rust-colored spots |
| Lobe color of compound tepal | Yellow (7B, RHS) |
| Lobe development of compound tepal | Developed |
| Free tepal color | Translucent White |
| Free tepal shape | Oval |
| Free tepal appearance | Simple folding under the apex |
| Free tepal apex development | Developed |
| Free tepal apex shape | Triangular |
| Anther exertion | Exerted |
| Filament color | Greyed-White (156B, RHS) |
| Anther color | Green-White (157C, RHS) |
| Pollen sacs color | Greyed-Green (196D, RHS) |
| Pollen vitality | Abundant |
| Style basic color | Greyed-White (196D, RHS) |
| Pigmentation on style | Without pigmentation |
| Style exertion | Exerted |
| Style shape | Curved at the base |
| Stigma color | Yellow-Orange (20B, RHS) |
| Ovary shape | Arched |
| Ovary basic color | Green-White (157B, RHS) |

TABLE 1-continued

| Botanical Description of 'HG07' | |
|---|---|
| Ovary pigmentation | Very few or no visible signs of pigmentation |
| The dominant color of male flower | Green-White (157D, RHS) |
| Irregular flowers | Absent |
| Arrangement of ovules | Two rowed |
| Fruit position | Parallel to the stalk |
| Number of fruits observed on the mid-hand of the bunch | ≥17, specifically between 120 and 140 fingers per bunch |
| Fruit length | ≤15 cm (12 to 15 cm) |
| Fruit diameter | 8 to 10 cm |
| Fruit shape (longitudinal curvature) | Curved (sharp curve) |
| Transverse section of fruit | Pronounced ridged |
| Fruit apex | Bottle-necked |
| Average weight of a fruit | 150 g |
| Average weight of bunch of fruit | 21 kg |
| Average number of bunches per plant | One |
| Remains of flower relicts at the fruit apex | Persistent style |
| Fruit pedicel length | 11 to 20 mm |
| Fruit pedicel width | >10 mm |

TABLE 1-continued

| Botanical Description of 'HG07' | |
|---|---|
| Average fruit pedicel width | 5 cm |
| Pedicel surface | Hairy |
| Fusion of pedicel | Very partially or no visible sign of fusion |
| Immature fruit peel color | Green (143C, RHS) |
| Mature fruit peel color | Yellow-Orange (16B, RHS) |
| Fruit peel thickness | ≥3 (3 to 5) mm |
| Adherence to the fruit peel | Fruit peels easily |
| Cracks in fruit peel | Without Cracks |
| Pulp in fruit | With pulp |
| Pulp color before maturity | Yellow-Green (150D, RHS) |
| Pulp color at maturity | Yellow (13D, RHS) |
| Fruits fall from hands. | No finger drop |
| Flesh texture | Firm (hard texture) |
| Predominant taste | Sweet (like Cavendish) |
| Presence of seed with the source of pollen | Without seeds |

The invention claimed is:

1. A new and distinct variety of banana plant named 'HG07', substantially as illustrated and described herein.

* * * * *

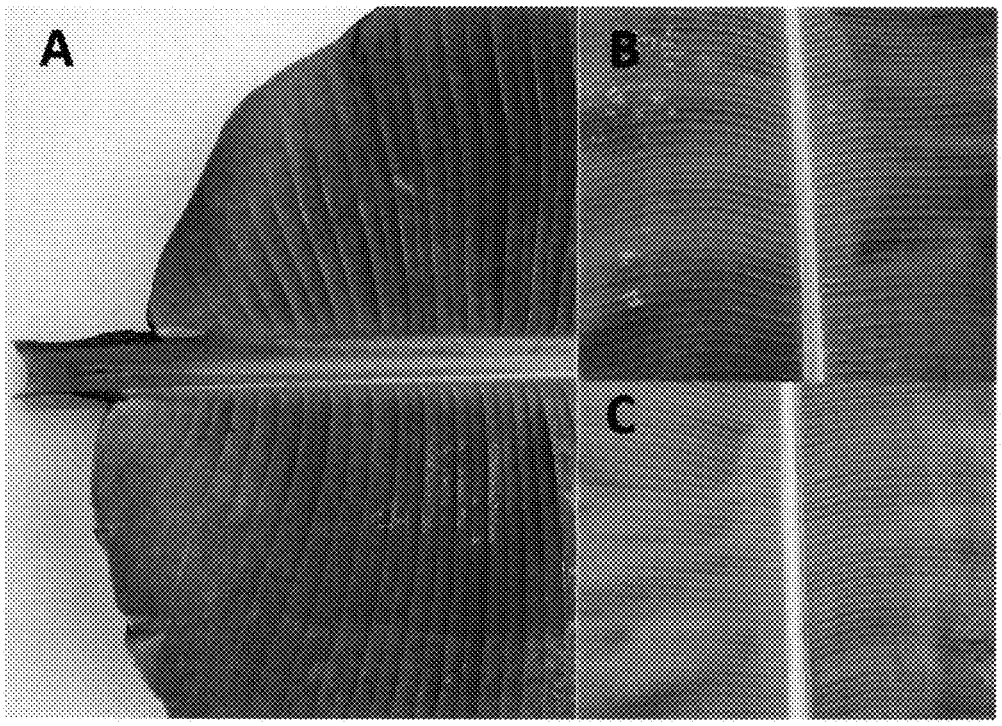
FIGS. 3A, 3B, & 3C
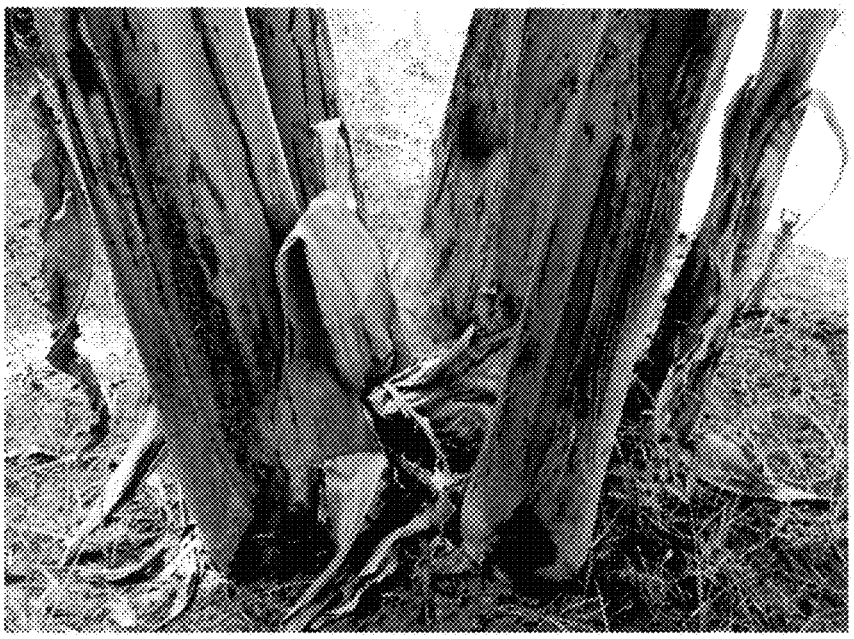
FIG. 4

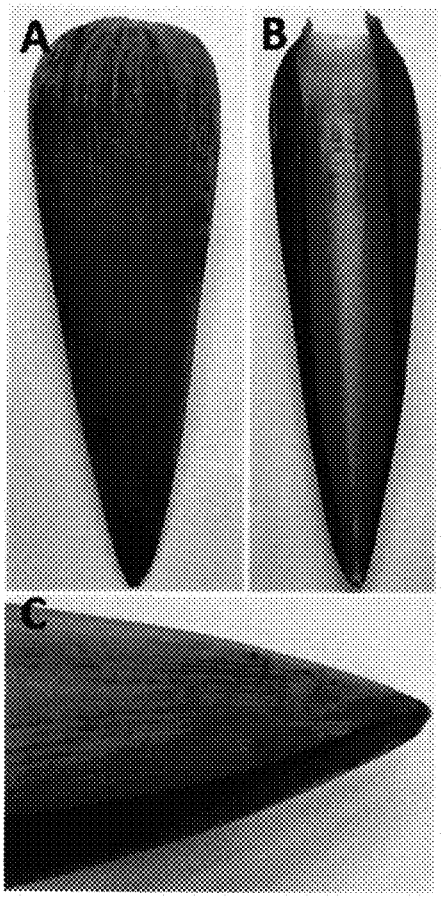
FIGS. 7A, 7B, & 7C
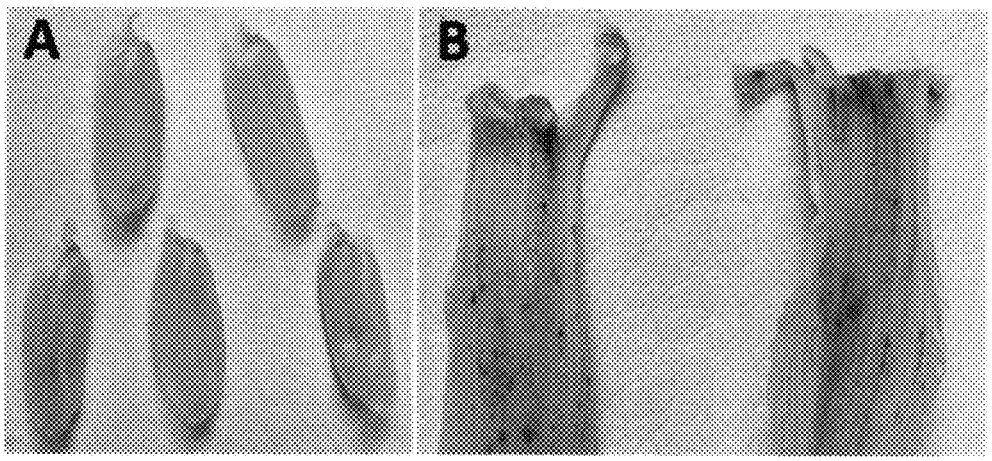
FIG. 8